(12) United States Patent
Park et al.

(10) Patent No.: US 7,491,347 B2
(45) Date of Patent: Feb. 17, 2009

(54) TI PRECURSOR, METHOD OF PREPARING THE SAME, METHOD OF PREPARING TI-CONTAINING THIN LAYER BY EMPLOYING THE TI PRECURSOR AND TI-CONTAINING THIN LAYER

(75) Inventors: Sung-ho Park, Seongnam-si (KR); Jung-hyun Lee, Yongin-si (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 535 days.

(21) Appl. No.: 11/282,486

(22) Filed: Nov. 21, 2005

(65) Prior Publication Data

US 2006/0157861 A1 Jul. 20, 2006

(30) Foreign Application Priority Data

Jan. 19, 2005 (KR) .................. 10-2005-0005027

(51) Int. Cl.
*H01B 1/06* (2006.01)
*H01B 1/02* (2006.01)
*C22C 14/00* (2006.01)

(52) U.S. Cl. ............... 252/507; 252/519.12; 420/417

(58) Field of Classification Search ............ None
See application file for complete search history.

(56) References Cited

U.S. PATENT DOCUMENTS

2004/0083963 A1 5/2004 Dando et al.

FOREIGN PATENT DOCUMENTS

| EP | 0 088 562 A2 | 9/1983 |
|---|---|---|
| KR | 2002-0016748 A | 3/2002 |

OTHER PUBLICATIONS

Raush, Marvin et al. Synthetic and Structure Studied on Carboxy, Carbomethoxy, and (n5-Cyclopentadienyl)(n7-Cycloheptatrienyl) Titanium, 1991, American Chemical Society, Organometallics vol. 10, No. 6, pp. 2084-2086.*
Koutsopoulos, S. et al. Inhibition of Hydroxyapatite Crystal Growth by Substituted Titanocenes, Jul. 6, 2000, American Chemical Society, Langmuir vol. 16, No. 16, pp. 6745-6749.*

* cited by examiner

*Primary Examiner*—Jennifer McNeil
*Assistant Examiner*—Sarah Van Oudenaren
(74) *Attorney, Agent, or Firm*—Buchanan Ingersoll & Rooney PC (57) ABSTRACT

A Ti-precursor for forming a Ti-containing thin layer represented by the formula I below, a method of preparing the same, a method of preparing a Ti-containing thin layer by employing the Ti-precursor and the Ti-containing thin layer are provided:

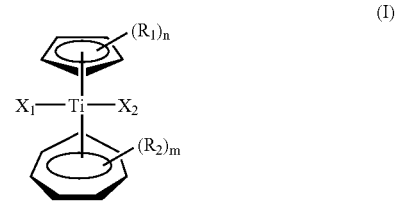

wherein
$X_1$ and $X_2$ are independently F, Cl, Br or I; n is 0, 1, 2, 3, 4 or 5; m is 0, 1, 2, 3, 4, 5, 6 or 7; and $R_1$ and $R_2$ are independently a linear or branched $C_{1-10}$ alkyl group. The Ti precursor for forming the Ti-containing thin layer can be deposited at a deposition temperature of approximately 150° C.~200° C., and a Ti-containing thin layer with a high performance character can be prepared.

21 Claims, 5 Drawing Sheets

TI PRECURSOR, METHOD OF PREPARING THE SAME, METHOD OF PREPARING TI-CONTAINING THIN LAYER BY EMPLOYING THE TI PRECURSOR AND TI-CONTAINING THIN LAYER

CROSS-REFERENCE TO RELATED PATENT APPLICATION

This application claims the benefit of Korean Patent Application No. 10-2005-0005027, filed on Jan. 19, 2005, in the Korean Intellectual Property Office, the disclosure of which is incorporated herein in its entirety by reference.

BACKGROUND OF THE DISCLOSURE

1. Field of the Disclosure

The present disclosure relates to a Ti-precursor, a method of preparing the same, a method of preparing a Ti-containing thin layer by using the Ti-precursor and the Ti-containing thin layer, and more particularly, to a Ti-precursor which can be deposited at low temperatures, a method of preparing the same, a method of preparing a Ti-containing thin layer by using the Ti-precursor and the Ti-containing thin layer.

2. Description of the Related Art

A semiconductor technology has been progressed continuously by pursuing more improved technology through miniaturizing semiconductor devices, and research on a process using a thin layer material suitable for such miniaturization is actively progressing.

Particularly, a Ti-containing thin layer is being employed in several fields for semiconductor devices.

For example, a $TiO_2$ thin layer for high density-dynamic random access memory (DRAM) is a thin layer having the highest dielectric constant of monolayers, and can be employed as various insulating layers. A TiN thin layer can be employed as a lower electrode in the high density-DRAM. Further, a TiN thin layer can be employed as an interconnection metal, for example, an adhesion layer for depositing Cu, etc.

Further, the Ti-containing thin layer includes a barium strontium titanate (BST) thin layer which can be used in a capacitor for DRAM, a lead zirconate titanate (PZT) thin layer which can be used in a ferroelectric random access memory (FRAM), a strontium bismuth titanate (SBT) thin layer, a bismuth lanthanum titanate (BLT) thin layer, etc.

There are diverse methods of preparing such Ti-containing thin layers. Of those methods, chemical vapor deposition (CVD) employing a Ti precursor is a process in which after the Ti precursor is vaporized, the desired thin layer made of solid material is synthesized through chemical reaction. The process can control forming a final thin layer at the molecular level. Further, a thin layer that has excellent large-area uniformity, can be applied over a large area, and an excellent step coverage on the surface of a substrate without damage, can be obtained.

A Ti precursor used in the CVD is described in, for example, Korean Patent Laying-Open No. 2002-0016748. The Ti precursor of the patent application consists of a tridentate ligand having valence of –2, and Ti.

Such a Ti precursor should satisfy various requirements such as high vapor pressure, high purity, low deposition temperature, high deposition rate, ease to handle, non-toxicity, and low cost, etc.

Figure 1:
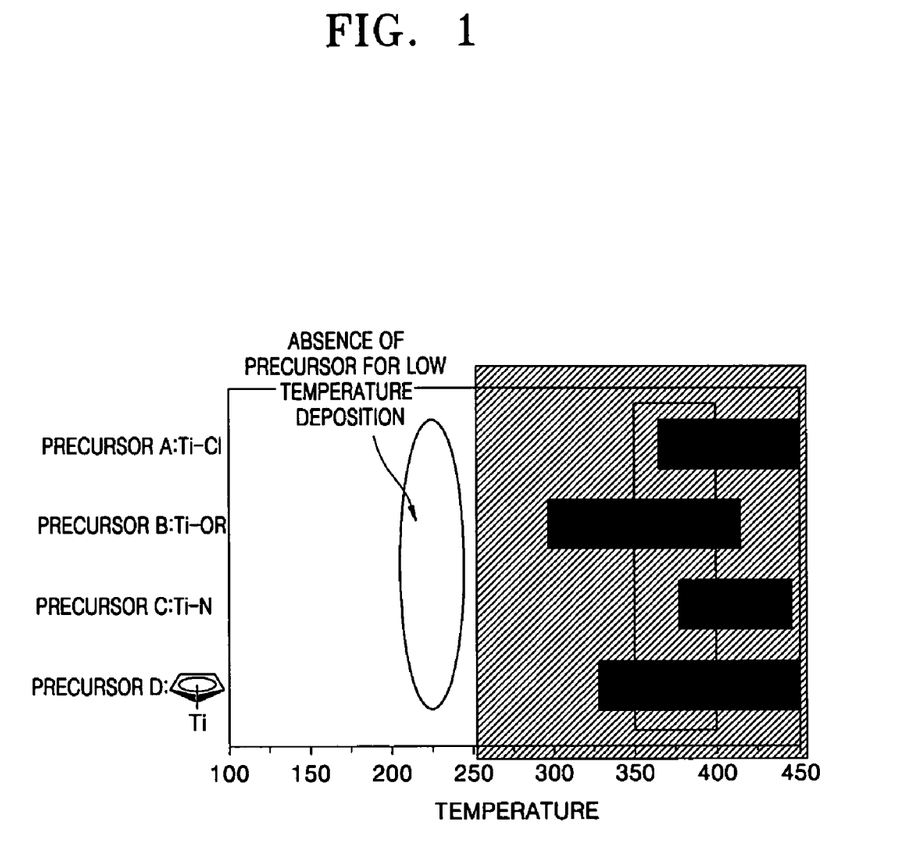
FIG. 1 shows schematically the deposition temperature range for conventional Ti precursors.

FIG. 1 shows conventional Ti precursors and their respective deposition temperatures. Referring to FIG. 1, in order to form a Ti-containing thin layer, the precursor A requires deposition temperatures of more than about 360° C., the precursor B requires deposition temperatures of more than about 300° C., the precursor C requires deposition temperatures of more than about 375° C., the precursor D requires deposition temperatures of more than about 330° C.

As described above, when conventional precursors are employed, a range of high deposition temperatures is required in order to form a Ti-containing thin layer having an electrical property suitable for application in various devices. However, this may result in damage in devices by the high temperature, and an increase in production costs and process time. Accordingly, a novel Ti precursor that can be deposited at low temperatures is needed.

SUMMARY OF THE DISCLOSURE

The present invention may provide a Ti precursor that can be deposited at low temperatures, e.g., about 150° C.~200° C.

The present invention also may provide a method of preparing the Ti precursor, a method of preparing a Ti-containing thin layer by employing the Ti precursor and the Ti-containing thin layer.

According to an aspect of the present invention, there is provided a Ti precursor for preparing a Ti-containing thin layer represented by formula I below:

(I)

wherein

$X_1$ and $X_2$ are independently F, Cl, Br or I;

n is 0, 1, 2, 3, 4 or 5;

m is 0, 1, 2, 3, 4, 5, 6 or 7; and $R_1$ and $R_2$ are independently a linear or branched $C_{1-10}$ alkyl group.

According to another aspect of the present invention, there is provided a method of preparing a Ti precursor for forming a Ti-containing thin layer represented by formula I below comprising reacting a Ti-containing compound represented by formula III below with a $C_7$-aromatic compound represented by formula IV below:

(I)

wherein $X_1$ and $X_2$ are independently F, Cl, Br or I;

n is 0, 1, 2, 3, 4 or 5;

m is 0, 1, 2, 3, 4, 5, 6 or 7; and $R_1$ and $R_2$ are independently a linear or branched $C_{1-10}$ alkyl group;

(III)

wherein
$X_3$, $X_4$ and $X_5$ are independently F, Cl, Br or I;
p is 0, 1, 2, 3, 4 or 5;
$R_3$ is a linear or branched $C_{1-10}$ alkyl group; and (IV)

wherein
q is 0, 1, 2, 3, 4, 5, 6 or 7; and
$R_4$ is a linear or branched $C_{1-10}$ alkyl group.

According to still another aspect of the present invention, there is provided a method of preparing a Ti-containing thin layer comprising of depositing a Ti precursor for forming a Ti-containing thin layer represented by the formula I at a deposition temperature of approximately 150° C.~200° C.

According to still yet another aspect of the present invention, there is provided a Ti-containing thin layer prepared by utilizing the method of preparing a Ti-containing thin layer identified above.

By employing a Ti precursor according to the present invention, a Ti-containing thin layer can be formed at low a deposition temperature, particularly, at approximately 150° C.~200° C. The Ti-containing thin layer has an excellent electrical property suitable for application in various devices.

BRIEF DESCRIPTION OF THE DRAWINGS

The above and other features and advantages of the present invention are described in detail in exemplary embodiments thereof with reference to the attached drawings in which.

DETAILED DESCRIPTION OF EXEMPLARY EMBODIMENTS

The present invention will now be described more fully hereinafter with reference to the accompanying drawings, in which preferred embodiments of the invention are shown. This invention may, however, be embodied in many different forms and should not be construed as being limited to the embodiments set forth herein. Rather, these embodiments are provided for exemplary purposes, and will more fully convey the invention to those skilled in the art. Like numbers refer to like elements throughout the specification.

A Ti precursor for forming a Ti-containing thin layer according to the present invention can be represented by formula I below:

(I)

wherein
$X_1$ and $X_2$ are independently F, Cl, Br or I;
n is 0, 1, 2, 3, 4 or 5;
m is 0, 1, 2, 3, 4, 5, 6 or 7; and
$R_1$ and $R_2$ are independently a linear or branched $C_{1-10}$ alkyl group.

According to the formula I, the Ti in the Ti precursor according to the present invention is substituted (i.e., when m is 1, 2, 3, 4, 5, 6 or 7) with a linear or branched $C_{1-10}$ alkyl group, or is an unsubstituted (i.e., when m is 0) $C_7$-aromatic ring moiety. Without having bound to a particular theory, the $C_7$-aromatic ring moiety can be a stable 6-membered π electron cation satisfying (4n+2) of Huckel, or an unstable 8-membered π electron anion. Accordingly, the binding force between the $C_7$-aromatic moiety and the Ti is so weak that the Ti precursor according to the present invention can be decomposed with relatively low energy. For this reason, the Ti precursor represented by the formula I can be deposited at a low deposition temperature, e.g., approximately 150° C.~200° C., and thus a Ti-containing thin layer having excellent performance, particularly excellent electrical property can be formed.

In the formula I, when n is 0, hydrogen atoms in $C_5$-aromatic ring moiety bound to Ti are unsubstituted. When n is 1, 2, 3, 4 or 5, the hydrogen atoms numbering 1, 2, 3, 4 or 5 among 5 hydrogen atoms in the $C_5$-aromatic ring moiety are substituted with $R_2$. The $R_2$ is a linear or branched $C_{1-10}$ alkyl group, for example, methyl, ethyl, isopropyl, n-butyl, hexyl group, etc.

In the formula I, when m is 0, hydrogen atoms in $C_7$-aromatic ring moiety bound to Ti are unsubstituted. When m is 1, 2, 3, 4, 5, 6 or 7, the hydrogen atoms numbering 1, 2, 3, 4, 5, 6 or 7 among 7 hydrogen atoms in the $C_7$-aromatic ring moiety are substituted with $R_2$. The $R_2$ is a linear or branched $C_{1-10}$ alkyl group, for example, methyl, ethyl, isopropyl, n-butyl, hexyl group, etc.

In the formula I, n may be 0 or 1; m may be 0 or 1; and R$_1$ and R$_2$ may be independently isopropyl or n-butyl group.

The Ti precursor of the formula I may be represented by formula II below:

(II)

By employing the Ti precursor, a Ti-containing thin layer can be formed at low a deposition temperature of approximately 150° C.~200° C., and the Ti-containing thin layer has an excellent electrical property suitable for application in various devices.

When a conventional Ti precursor for forming a Ti-containing thin layer (for example, precursors as depicted in FIG. 1) is deposited at a deposition temperature of approximately 150° C.~200° C., at which the Ti precursor according to the present invention can be deposited, to form a Ti-containing thin layer, the Ti-containing obtained therefrom has a poor electrical property, particularly current leakage, and thus is difficult to apply to various devices such as a semiconductor. However, the Ti precursor according to the present invention can form a Ti-containing thin layer at a low deposition temperature of approximately 150° C.~200° C., and the Ti-containing thin layer obtained therefrom has an excellent electrical property that a Ti-containing thin layer obtained while utilizing high deposition temperatures (e.g., above 300° C.) can possess.

Accordingly, when various devices including a Ti-containing thin layer are prepared, the deterioration of the devices by heat, that is experienced when depositing the Ti-containing thin layer, can be minimized. Thus, the reliability for the devices can be enhanced, and the production cost and process time for forming the Ti-containing thin layer can be reduced. Further, the Ti precursor has low evaporation and deposition temperatures compared to a conventional Ti precursor, and is more amenable to deposit together with precursors of other atoms having low deposition temperatures, for example, a Pb precursor, a Zr precursor, a Bi precursor or a La precursor.

The excellent electrical property of the Ti-containing thin layer obtained from depositing the Ti precursor according to the present invention at a low deposition temperature of approximately 150° C.~200° C. can be confirmed in the evaluation examples set forth below.

A method of preparing the Ti precursor represented by the formula I comprises reacting a Ti-containing compound represented by formula III below with a C$_7$-aromatic compound represented by formula IV below:

(III)

wherein
X$_3$, X$_4$ and X$_5$ are independently F, Cl, Br or I;

p is 0, 1, 2, 3, 4 or 5;
R$_3$ is a linear or branched C$_{1-10}$ alkyl group; and (IV)

wherein
q is 0, 1, 2, 3, 4, 5, 6 or 7; and
R$_4$ is a linear or branched C$_{1-10}$ alkyl group.

The starting materials of the Ti precursor represented by the formula I are the Ti-containing compound represented by the formula III and the C$_7$-aromatic compound represented by the formula IV.

In the formula III, p may be 0 or 1, and R$_3$ may be isopropyl or n-butyl group; and in the formula IV, q may be 0 or 1, R$_4$ may be isopropyl or n-butyl group.

The above reaction is carried out in the presence of the catalyst, and the catalyst includes a material usually referred to Grignard reagent. The Grignard reagent may be obtained from a chemical supply company, or synthesized by employing a method of preparing the Grignard reagent that is well known to those skilled in the art. The Grignard reagent may be represented by the formula of i-PrMgCl (wherein i-Pr is isopropyl group). The Grignard reagent is a strong base, having a strong nucleophilic property, and thus can promote the reaction of the Ti-containing compound with the C$_7$-aromatic compound.

The temperature of the reaction between the Ti-containing compound represented by the formula III and the C$_7$-aromatic compound represented by the formula IV may be, for example, −78° C., and the reaction time may be, for example, 12 hours. The reaction atmosphere may be, for example, a nitrogen atmosphere.

The method of preparing the Ti-containing thin layer according to the present invention comprises depositing the Ti-precursor for forming the Ti-containing thin layer represented by the formula I at a deposition temperature of approximately 150° C.~200° C. The method of preparing the Ti-containing thin layer can employ as a metal precursor solely the Ti precursor represented by the formula I, or other precursor, for example, at least one precursor selected from the group consisting of a Pb precursor, a Zr precursor, a Bi precursor and a La precursor, together with the Ti precursor represented by the formula I. The metal precursors other than the Ti precursor are known to those skilled in the art, and are not particularly limited.

As mentioned above, since the Ti precursor represented by the formula I has weak binding force between the Ti and the C$_7$-aromatic ring moiety, the Ti precursor can be deposited at a relatively low temperature, for example, approximately 150° C.~200° C., preferably approximately 160° C.~190° C., and most preferably approximately 180° C. to form a Ti-containing thin layer. Such deposition temperatures are remarkably low ones in view of the fact that a conventional Ti precursor requires deposition temperatures of above 300° C., i.e., the conventional Ti precursor could not form a Ti-containing thin layer having the desired electrical property at deposition temperatures of below 200° C.

Particularly, according to an embodiment of the method of preparing the Ti-containing thin layer, the method can com prise depositing the Ti precursor for forming a Ti-containing thin layer represented by the formula II below:

(II)

Cl—Ti—Cl

In the method of preparing a Ti-containing thin layer according to the present invention, the depositing step can employ, for example, chemical vapor deposition (CVD), particularly atomic layer deposition (ALD), but the examples are not limited these. The CVD and ALD can be performed in various manners known to the art. The ALD includes plasma enhanced atomic layer deposition (PEALD). A more detailed description for the chemical vapor deposition or the atomic layer deposition is disclosed in Korean Patent Laying-Open No. 2003-0079181, 2001-0033532 and 2002-0084616. The chemical vapor deposition or the atomic layer deposition in the patent applications is incorporated for the reference in the specification of the present invention. Particularly, the atomic layer deposition is known as a deposition method that can enhance the accuracy of step coverage.

The Ti-containing thin layer according to the present invention is a thin layer that is prepared by depositing the Ti precursor identified above at a low temperature, particularly 150° C.~200° C. The Ti-containing thin layer refers to a thin layer comprising Ti element. It can be understood that although the thickness of the Ti-containing thin layer varies depending on the nature of the devices including it, the thickness typically is in the range of dozens Å to thousands Å.

The Ti-containing thin layer may be, for example, $TiO_2$ thin layer or TiN thin layer. The $TiO_2$ thin layer can be obtained, for example, by depositing the Ti precursor according to the present invention in the presence of a transporting gas, such as $O_2$, $H_2O$ or $O_3$. The TiN thin layer can be obtained, for example, by depositing the Ti precursor according to the present invention in the presence of a transporting gas, such as $NH_3$.

Further, the thin layer may be, but not limited to, a barium strontium titanate (BST), a lead zirconate titanate (PZT), a strontium bismuth titanate or a bismuth lanthanum titanate, etc., formed by employing precursors of atoms other than Ti, for example, a Ba precursor, a St precursor, a Pb precursor, a Zr precursor, a Bi precursor or a La precursor.

Devices including the Ti-containing thin layer formed by employing the Ti precursor mentioned above can be protected from excessive heat present when depositing a Ti-containing thin layer, and thus the reliability for devices can be enhanced.

The present invention will be described in greater detail with reference to the following examples. The following examples are for illustrative purposes and are not intended to limit the scope of the invention.

EXAMPLES

Example

Synthesis of Ti Precursor

Reaction Embodiment I formula VI        formula VII        formula II

In accordance with the reaction Embodiment I, the Ti-precursor represented by the formula II was synthesized. The solvent utilized was dry ether. $C_7C_8$ represented by the formula VII (available from Aldrich company) (17 g, 188 mmole) and Grignard reagent (synthesized by a known technique) (14 mmole) represented by i-PrMgBr (7 ml, 2M) were added to $C_5H_5TiCl_3$ represented by the formula VI (available from Aldrich company) (10 g, 46 mmole) at a low temperature, −78° C., and then the mixture was reacted from −78° C. to ambient temperature for 12 hours. After completion of the reaction, volatile materials of the reaction products were removed with reduced pressure, the residues were extracted with dry propane, and then the extracts were recrystalized with pentane to obtain 1.26 g (yield of 10%) of the Ti precursor represented by the formula II as a sky-blue crystal. The NMR analysis and MS analysis for the Ti precursor were performed.

Figure 2:
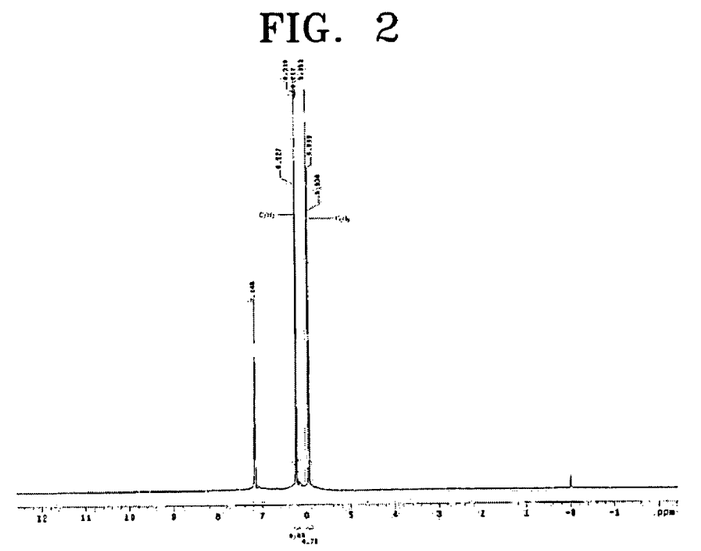
FIGS. 2 and 3 are NMR analysis data for an embodiment of the Ti precursor according to the present invention.

$^1$H NMR($C_6D_6$, 200 MHz) analysis for the Ti precursor was performed and the results are as follows. The NMR data are shown in FIG. 2. The results of the analysis for NMR peak are as follows: 5.98 ppm(5H), 6.23 ppm(7H).

Figure 3:
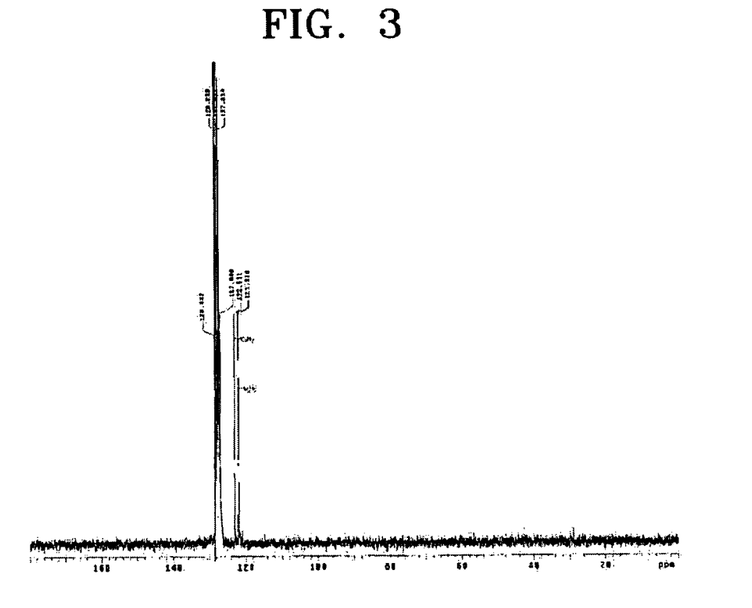

$^{13}$C NMR($C_6D_6$, 200 MHz) analysis for the Ti precursor was performed and the results are as follows. The NMR data are shown in FIG. 3. The results of the analysis for NMR peak are as follows: 121 ppm(5C), 121 ppm(7C).

Figure 4:
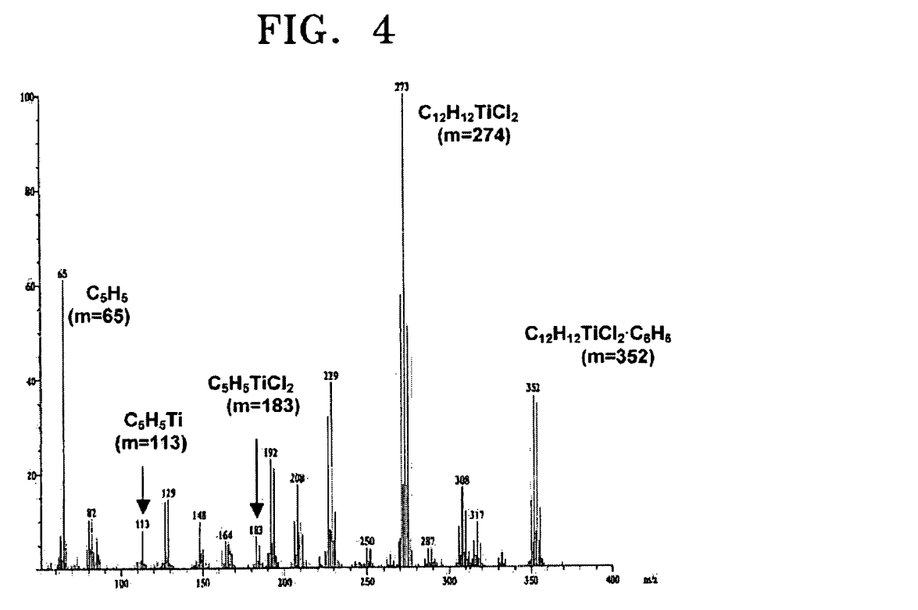
FIG. 4 is mass analysis data for an embodiment of the Ti precursor according to the present invention.

A mass analysis (El mass, JEOL JMS600) for the Ti precursor was performed and the results are as follows. The MS data are shown in FIG. 4. The results of the analysis for MS peak are as follows: main peak, m/e 274.

Evaluation Example 1

Evaluation for Sublimation Characteristics

The sublimation characteristics for the Ti precursor (hereinafter refers to "precursor 1") synthesized from the example were evaluated. The evaluation for sublimation characteristics was performed by employing a suction sublimer.

From the evaluation results for the sublimation characteristics, it can be seen that the sublimation temperature of the precursor 1 was 120° C. at 0.1 torr. Accordingly, it can be found that the precursor 1 according to the present invention can be sublimated at relatively low temperatures.

Evaluation Example 2

Figure 5:
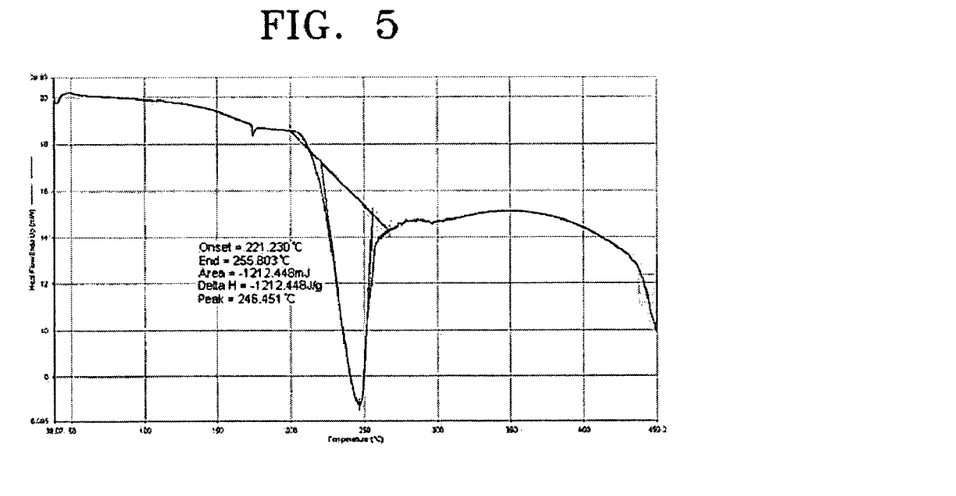
FIG. 5 is DSC (Differential Scanning Calorimetry) analysis data for an embodiment of the Ti precursor according to the present invention under a nitrogen atmosphere.

DSC (Differential Scanning Calorimetry) Analysis Under a Nitrogen Atmosphere The DSC analysis for the precursor 1 was performed at atmospheric pressure under a nitrogen atmosphere and the results are shown in FIG. 5. For the DSC analysis, Netzsch STA 449C equipment was employed, and DSC analysis for the precursor 1 was measured up to 450° C. with the temperature rise rate of 10° C./min, a nitrogen flux of 20 ml/min and an oxygen flux of 30 ml/min.

Referring to FIG. 5, the pyrolysis temperature of the precursor 1 was very low, i.e., about 245° C.

Evaluation Example 3

DSC Analysis Under Atmosphere

Figure 6:
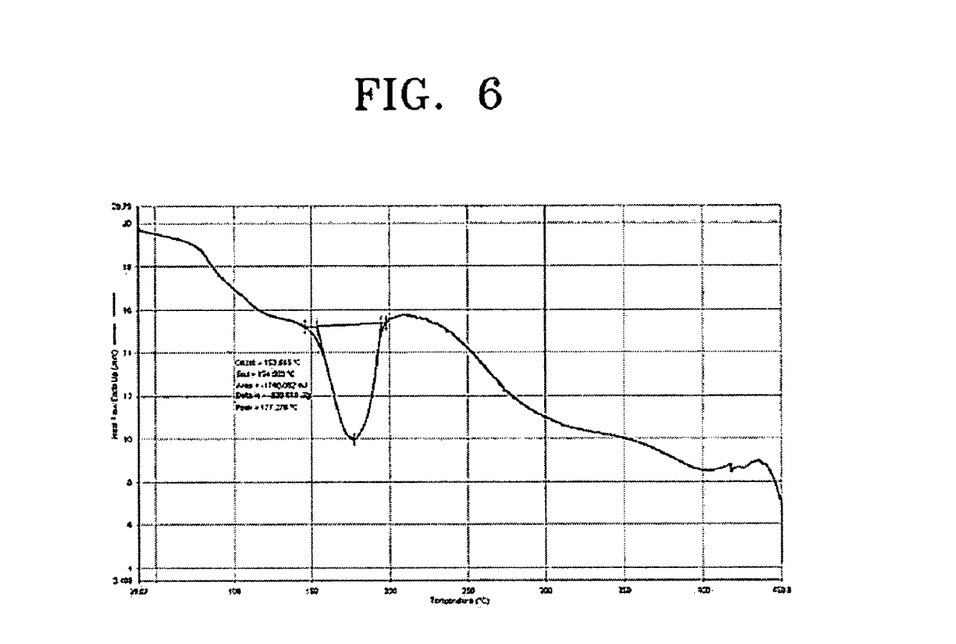
FIG. 6 is DSC analysis data for an embodiment of the Ti precursor according to the present invention under atmosphere.

The DSC analysis for the precursor 1 was performed under atmosphere and its results are shown in FIG. 6. The method and conditions of the DSC analysis are the same as described in the evaluation example 2.

Referring to FIG. 6, the pyrolysis temperature of the precursor 1 by oxygen and heat was very low, i.e., about 175° C.

Preparation Example

Forming TiO$_2$ Thin Layer by ALD Method

A multilayer consisting of Si/SiO$_2$/Ru(500 Å) as a substrate for forming TiO$_2$ thin layer was prepared, and then a TiO$_2$ thin layer having a thickness of 100 Å was formed on the upper part of the Ru layer by employing precursor 1. IPS (Integrated Process Systems) equipment was employed as the ALD equipment for forming the TiO$_2$ thin layer by the ALD method. The deposition conditions were as follows:

TABLE 1

| Deposition pressure | 0.25 torr |
|---|---|
| Flux of transporting gas O$_3$ | 500 sccm |
| Flux of Ti precursor | 300 sccm |
| Substrate temperature | 180° C. |
| Evaporation temperature of Ti precursor | 120° C. |
| Deposition time | 20 min |

Figure 7:
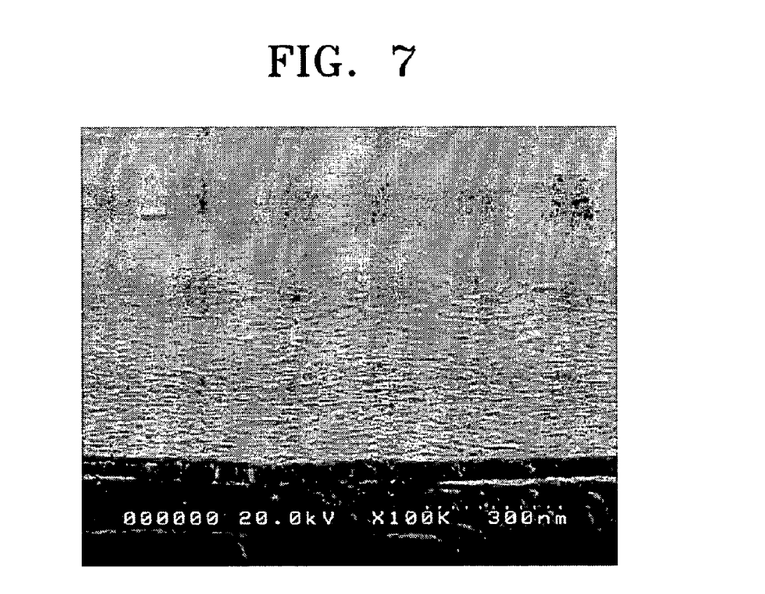
FIG. 7 is a SEM photograph of $TiO_2$ thin layer prepared by depositing an embodiment of the Ti precursor according to the present invention at a deposition temperature of 180° C.

The obtained section of TiO$_2$ thin layer was observed as a TEM photograph, and the results are shown in FIG. 7. Referring to FIG. 7, it can be seen that a thin layer with uniform thickness was formed in spite of the use of a low deposition temperature, i.e., 180° C. as described in the table 1. Then, a device having an MIM (metal-insulator-metal) structure was formed upon forming a Ru layer in the thickness 300 Å on the upper part of the TiO$_2$ layer. The device is referred to Sample 1.

Evaluation Example 4

Evaluation of the Tox (Thickness of Oxide) for Sample 1

Figure 8:
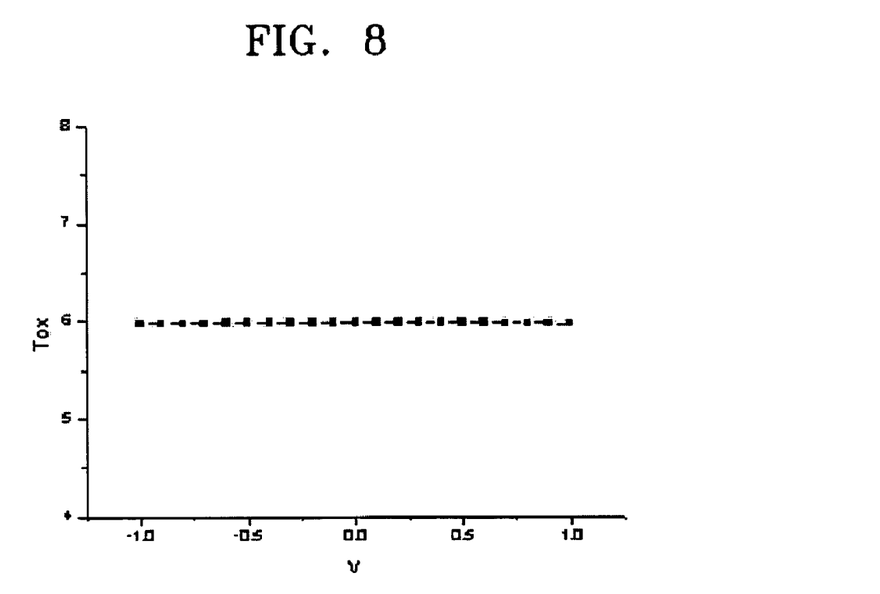
FIG. 8 is a graph showing the Tox (thickness of oxide) characteristic of $TiO_2$ thin layer prepared by depositing an embodiment of the Ti precursor according to the present invention at a deposition temperature of 180° C.

The Tox (thickness of oxide) for the sample 1 was evaluated and its results are shown in FIG. 8. The Tox evaluation was performed by measuring the capacitance-voltage (C-V) characteristics and current-voltage (I-V) characteristics for the Sample 1 by using HP4284B and HP4156C semiconductor parameter analyzers, respectively.

Referring to FIG. 8, it can be seen that the Tox for the Sample 1 was very low, i.e., about 6.

Evaluation Example 5

Evaluation of the Leakage Current for Sample 1

Figure 9:
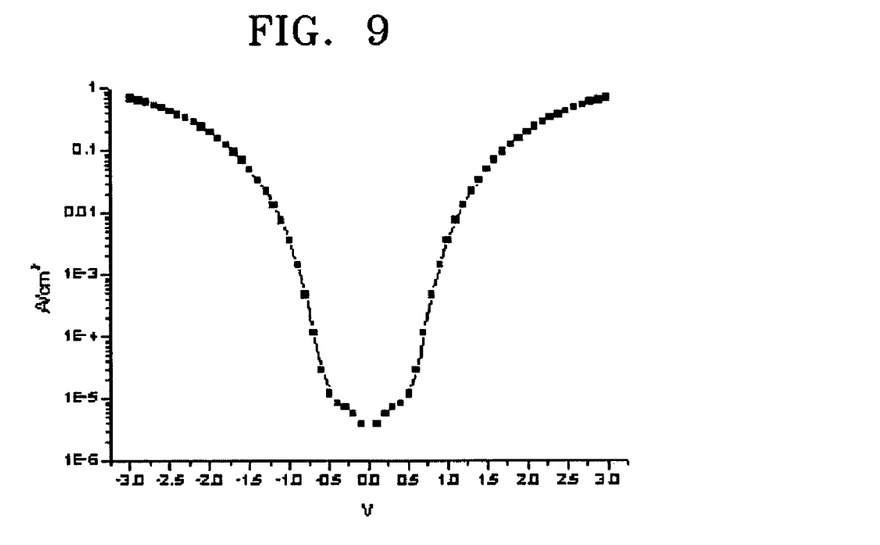
FIG. 9 is a graph showing the leakage current characteristic of $TiO_2$ thin layer prepared by depositing an embodiment of the Ti precursor according to the present invention at a deposition temperature of 180° C.

The leakage current for the Sample 1 was evaluated by employing an ammeter and the results are shown in FIG. 9.

Referring to FIG. 9, it can be seen that the current leakage for the Sample 1 according to the present invention was very low in spite of very low Tox for the Sample 1 as found in the evaluation Example 4.

Effect of the Present Invention

The Ti precursor according to the present invention for forming a Ti-containing thin layer can be deposited at a low deposition temperature, for example, approximately 150° C.~200° C., and the Ti-containing thin layer obtained therefrom has an excellent electrical property suitable for application in various devices. Accordingly, when various devices including a Ti-containing thin layer are prepared, damage of the devices by heat, that is experienced when depositing the Ti-containing thin layer, can be minimized, and the production costs and process time can be reduced. Furthermore, various types of the Ti-containing thin layers can be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A Ti precursor for preparing a Ti-containing thin layer represented by formula I below:

(I)

wherein

X$_1$ and X$_2$ are independently F, Cl, Br or I;

n is 0, 1, 2, 3, 4 or 5;

m is 0, 1, 2, 3, 4, 5, 6 or 7; and

R$_1$ and R$_2$ are independently a linear or branched C$_{1-10}$ alkyl group.

2. The Ti precursor for preparing a Ti-containing thin layer according to claim 1, wherein n is 0 or 1; m is 0 or 1; and R$_1$ and R$_2$ are independently isopropyl or n-butyl group.

3. The Ti precursor for preparing a Ti-containing thin layer according to claim 1, wherein the precursor is represented by formula II below:

(II)

4. A method of preparing a Ti precursor for forming a Ti-containing thin layer represented by formula I below comprising reacting a Ti-containing compound represented by formula III below with a $C_7$-aromatic compound represented by formula IV below:

(I)

wherein
$X_1$ and $X_2$ are independently F, Cl, Br or I;
n is 0, 1, 2, 3, 4 or 5;
m is 0, 1, 2, 3, 4, 5, 6 or 7; and
$R_1$ and $R_2$ are independently a linear or branched $C_{1-10}$ alkyl group;

(III)

wherein
$X_3$, $X_4$ and $X_5$ are independently F, Cl, Br or I;
p is 0, 1, 2, 3, 4 or 5;
$R_3$ is a linear or branched $C_{1-10}$ alkyl group; and (IV)

wherein
q is 0, 1, 2, 3, 4, 5, 6 or 7; and
$R_4$ is a linear or branched $C_{1-10}$ alkyl group or $C_{6-15}$ aryl group.

5. The method of preparing a Ti precursor for forming a Ti-containing thin layer according to claim 4, wherein in the formula I, n is 0 or 1, m is 0 or 1, and $R_1$ and $R_2$ are independently isopropyl or n-butyl group; in the formula III, p is 0 or 1, and $R_3$ is isopropyl or n-butyl group; and in the formula IV, q is 0 or 1, $R_4$ is isopropyl or n-butyl group.

6. A method of preparing a Ti-containing thin layer comprising depositing the Ti-precursor for forming the Ti-containing thin layer represented by the formula I below at a deposition temperature of approximately 150° C.~200° C.:

(I)

wherein
$X_1$ and $X_2$ are independently F, Cl, Br or I;
n is 0, 1, 2, 3, 4 or 5;
m is 0, 1, 2, 3, 4, 5, 6 or 7; and
$R_1$ and $R_2$ are independently a linear or branched $C_{1-10}$ alkyl group.

7. The method of preparing a Ti-containing thin layer according to claim 6, wherein the method comprises depositing the Ti-precursor for forming the Ti-containing thin layer represented by the formula II below:

(II)

8. A Ti-containing thin layer prepared by employing the method of claim 7.

9. The Ti-containing thin layer according to claim 8, wherein the Ti-containing thin layer is $TiO_2$ thin layer or TiN thin layer.

10. The Ti-containing thin layer according to claim 8, wherein the Ti-containing thin layer is a barium strontium titanate (BST) thin layer, a lead zinconate titanate (PZT) thin layer, a strontium bismuth titanate thin layer or a bismuth lanthanum titanate thin layer.

11. The method of preparing a Ti-containing thin layer according to claim 6, wherein the depositing is performed by employing chemical vapor deposition (CVD).

12. The method of preparing a Ti-containing thin layer according to claim 11, wherein the chemical vapor deposition is performed by employing atomic layer deposition (ALD).

13. A Ti-containing thin layer prepared by employing the method of claim 12.

14. The Ti-containing thin layer according to claim 13, wherein the Ti-containing thin layer is $TiO_2$ thin layer or TiN thin layer.

15. The Ti-containing thin layer according to claim 13, wherein the Ti-containing thin layer is a barium strontium titanate (BST) thin layer, a lead zinconate titanate (PZT) thin layer, a strontium bismuth titanate thin layer or a bismuth lanthanum titanate thin layer.

16. A Ti-containing thin layer prepared by employing the method of claim 11.

17. The Ti-containing thin layer according to claim 16, wherein the Ti-containing thin layer is $TiO_2$ thin layer or TiN thin layer.

18. The Ti-containing thin layer according to claim 16, wherein the Ti-containing thin layer is a barium strontium titanate (BST) thin layer, a lead zinconate titanate (PZT) thin layer, a strontium bismuth titanate thin layer or a bismuth lanthanum titanate thin layer.

19. A Ti-containing thin layer prepared by employing the method of claim 6.

20. The Ti-containing thin layer according to claim 19, wherein the Ti-containing thin layer is $TiO_2$ thin layer or TiN thin layer.

21. The Ti-containing thin layer according to claim 19, wherein the Ti-containing thin layer is a barium strontium titanate (BST) thin layer, a lead zinconate titanate (PZT) thin layer, a strontium bismuth titanate thin layer or a bismuth lanthanum titanate thin layer.

* * * * *